US010386335B2

(12) United States Patent
Robert et al.

(10) Patent No.: US 10,386,335 B2
(45) Date of Patent: Aug. 20, 2019

(54) METHOD FOR PROCESSING SIGNALS FROM AN ULTRASOUND PROBE ACQUISITION, CORRESPONDING COMPUTER PROGRAM AND ULTRASOUND PROBE DEVICE

(71) Applicant: COMMISSARIAT A L'ENERGIE ATOMIQUE ET AUX ENERGIES ALTERNATIVES, Paris (FR)

(72) Inventors: Sebastien Robert, Le Kremlin-Bicetre (FR); Eduardo-Rigoberto Lopez Villaverde, Massy (FR); Julien Albertini, Levallois (FR); Leonard Lejeune, Montrouge (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 416 days.

(21) Appl. No.: 15/106,680

(22) PCT Filed: Dec. 15, 2014

(86) PCT No.: PCT/FR2014/053347

§ 371 (c)(1),
(2) Date: Aug. 22, 2016

(87) PCT Pub. No.: WO2015/092250

PCT Pub. Date: Jun. 25, 2015

(65) Prior Publication Data

US 2016/0349218 A1 Dec. 1, 2016

(30) Foreign Application Priority Data

Dec. 20, 2013 (FR) ...................... 13 63246

(51) Int. Cl.
*G01N 29/06* (2006.01)
*G01N 29/04* (2006.01)
(Continued)

(52) U.S. Cl.
CPC ......... *G01N 29/069* (2013.01); *G01N 29/043* (2013.01); *G01N 29/07* (2013.01);
(Continued)

(58) Field of Classification Search
CPC .... G01N 29/069; G01N 29/043; G01N 29/07; G01S 7/52047
(Continued)

(56) References Cited

U.S. PATENT DOCUMENTS

2011/0112404 A1* 5/2011 Gourevitch ............ A61B 5/417
600/443

OTHER PUBLICATIONS

Kotowick, Kyle. Rohling, Robert. Lampe, Lutz. "Adaptive compounding of synthetic aperture and compounded plane-wave imaging for fast utrasonography". 2013 IEEE International Symposium of Biomedical Imaging. Apr. 7-11, 2013. pp. 784-787 (Year: 2013).*
(Continued)

*Primary Examiner* — Tarun Sinha
(74) *Attorney, Agent, or Firm* — Oblon, McClelland, Maier & Neustadt, L.L.P.

(57) ABSTRACT

A method including control of M emission transducers for L successive ultrasound plane wave emissions having L different emission angles, control of N reception transducers for simultaneously receiving N measurement time signals for each emission and reconstitution of an imaged zone by calculating, at each point, a value resulting from a processing of the measurement time signals received. The reconstitution of the imaged zone includes calculating L'×N flight times, L'≤L, each flight time $t_{l,n}$ being the time taken for the l-th plane wave, the emission zone of which includes the point considered, where 1≤l≤L', to be received by the n-th reception transducer, where 1≤n≤N, passing through the point considered according to a predetermined propagation mode, and coherent summing L'×N instantaneous values taken, respectively, by the L'×N measurement time signals received corresponding to the L' emissions, at the L'×N flight times.

10 Claims, 5 Drawing Sheets

Figure 1:
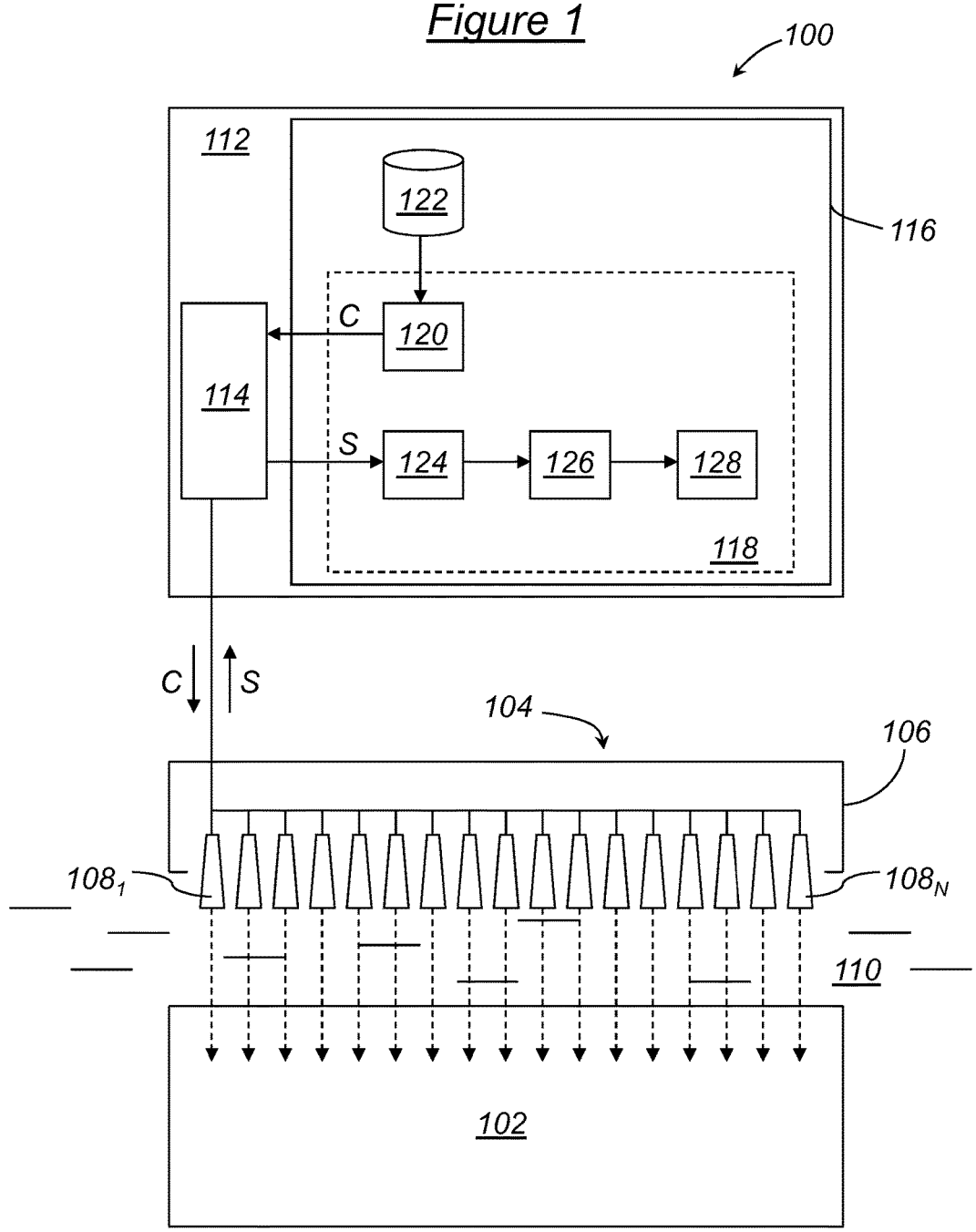

(51) Int. Cl.
  *G01N 29/07* (2006.01)
  *G01S 15/89* (2006.01)
  *G01S 7/52* (2006.01)
(52) U.S. Cl.
  CPC ...... *G01S 7/52047* (2013.01); *G01S 15/8915* (2013.01); *G01S 15/8997* (2013.01); *G01N 2291/011* (2013.01); *G01N 2291/106* (2013.01); *G01N 2291/262* (2013.01)
(58) Field of Classification Search
  USPC .......................................................... 73/598
  See application file for complete search history.

(56) References Cited

OTHER PUBLICATIONS

Mustafa Karaman, et al., "Synthetic Aperture Imaging for Small Scale Systems", IEE Transactions on Ultrasonics, Ferroelectrics, and Frequency Control, vol. 42, No. 3, May 1995, (14 pages).

Caroline Holmes, et al., "Post-processing of the full matrix of ultrasonic transmit-receive array data for non-destructive evaluation", NDT & E International, No. 38, 2005, (11 pages).

Gabriel Montaldo, et al., "Coherent Plane-Wave Compounding for Very High Frame Rate Ultrasonography and Transient Elastography", IEE transactions on Ultrasonic, Ferroelectrics, and Frequency Control, vol. 56, No. 3, XP011255897, Mar. 2009, (18 pages).

A. Fidahoussen, et al., "Imaging of Defects in Several Complex Configurations by Simulation-Helped Processing of Ultrasonic Array Data", Review of Quantitative Nondestructive Evaluation vol. 29, 2010, (8 pages).

Kyle Kotowick, et al., "Adaptive Compounding of Synthetic Aperture and Compounded Plane-Wave Imaging for Fast Ultrasonography", XP-002729342, International Symposium on Biomedical Imaging: From Nano to Macro, Apr. 2013, (4 pages).

P. Calmon, et al., "Model Based Reconstruction of UT Array Data", AIP Conference Proceedings, vol. 975, XP 055073257, 2008, (9 pages).

International Search Report dated Mar. 11, 2015 for PCT/FR2014/053347 filed on Dec. 15, 2014.

\* cited by examiner

METHOD FOR PROCESSING SIGNALS FROM AN ULTRASOUND PROBE ACQUISITION, CORRESPONDING COMPUTER PROGRAM AND ULTRASOUND PROBE DEVICE

This invention relates to a method for processing signals from an ultrasound probe acquisition for producing ultrasound imaging. It also relates to a corresponding computer program and ultrasound probe device.

The invention applies in particular to the field of non-destructive testing by ultrasound, wherein the acquisition of ultrasound signals makes it possible to view and detect defects in structures, but it may also be applied to any type of ultrasound echographic imaging, in particular in the medical field for examining zones of interest in the human or animal body.

It more specifically relates to a processing method acquiring ultrasound signals as follows:
- control of M emission transducers for L successive ultrasound wave emissions to a zone of interest,
- control of N receiving transducers so as to receive, simultaneously and for a predetermined duration, for each emission, N measurement time signals, measuring in particular echoes due to reflections of the emission considered in the zone of interest,
- reconstitution of an image of the zone of interest by calculating, at each point of a plurality of predetermined points of said zone of interest, a value resulting from a processing of at least some of the L×N measurement time signals received.

Such an acquisition is generally performed by means of a multi-element sensor probe device, wherein each transducer is both an emitter and a receiver, a switching between said two modes being capable of being controlled electronically. The sensor may be placed in contact with the object to be probed or at a distance, but in the latter case it must be immersed so as to ensure the transmission of ultrasound waves in the object to be probed. Said sensor may be linear (1D) or matricial (2D), for 2D or 3D imaging, with rigid or flexible elements.

In consideration of current processor calculation capacities, the reconstitution of the image of the zone of interest by processing of measurement time signals received may be provided on board in control instruments for real-time processing.

In practice, and according to a first family of acquisition techniques, the previously defined ultrasound acquisition, generally qualified as FMC (full matrix capture) acquisition, consists in emitting an ultrasound wave by exciting the first emission transducer and receiving echoes of said emission with the set of N reception transducers, then electronically switching in the set of emission transducers in order to excite them successively. The emission and reception transducers may be located on two distinct sensors, but when the same transducers perform the emission and reception functions, N×N measurement time signals are obtained.

In the article of C. Holmes et al, entitled "Post-processing of the full matrix of ultrasonic transmit-receive array data for non-destructive evaluation", published in NDT&E International 38 (available online on Jun. 15, 2005), pages 701-711, the N×N measurement time signals obtained are processed to produce a synthetic focusing of the "all-point focusing" type, enabling a high-resolution image of the zone of interest to be obtained.

More specifically, this synthetic focusing consists in calculating, for each point of the zone of interest, the flight times $T_{i,j}$ corresponding to the time of travel between each emission transducer (index i) and each reception transducer (index j), passing through the point considered (N×N flight times for each point). The synthetic focusing is performed by summing, for each point of the zone of interest, the amplitudes extracted from the measurement time signals received, denoted $K_{i,j}(t)$, at times $t=T_{i,j}$. The amplitude A at a point P of the image may therefore be written:

$$A(P)=|\Sigma_{i=1}^{N}\Sigma_{j=1}^{N}K_{i,j}[T_{i,j}(P)]|$$

The reconstruction by all-point focusing may be performed according to various known modes of ultrasound examination: the direct mode where the associated flight times are described above, and other more complex modes where the flight times include multiple reflections on the boundaries of the structure as well as conversions of modes between the longitudinal polarization waves and the transverse polarization waves. For a detailed explanation of said other more complex modes, it is possible in particular to refer to the article of A. Fidahoussen et al, entitled "Imaging of defects in several complex configurations by simulation-helped processing of ultrasonic array data", published in Review of Quantitative Nondestructive Evaluation, vol. 29 (2009), pages 847-854.

However, in the presence of electronic noise (due to the acquisition system) or structural noise (due to the nature of the material) on the measurement signals, the reconstruction by all-point focusing may provide images of lower quality by comparison with the classic echographic methods. The imaging by all-point focusing may also be significantly degraded when the material is attenuating, as is the case for example when examining aeronautical, rubber or tire composites, etc. This attenuation diminishes the amplitude of the ultrasound waves transmitted in the material as they are propagated so that the amplitude of the echoes received may be lower than the electronic noise. The advantage of classic echographic methods is that all of the transducers emit simultaneously by applying a predetermined delay law so as to focus on a given point. Conversely, in the FMC acquisition method generally implemented in order to then perform the reconstruction by synthetic focusing, each emission is performed by a single transducer, which limits the energy transmitted and the depth of penetration of the waves in the inspected part. This results in a reduction in the signal-to-noise ratio (SNR) on the resulting imaging, which may make it difficult to detect and characterize any defects. This reduction in the SNR is greater the higher the structural or electronic noise is.

A partial solution to this problem of reducing the SNR is provided in the article of M. Karaman et al, entitled "Synthetic aperture imaging for small scale systems", published in IEEE Transactions on Ultrasonics, Ferroelectrics, and Frequency Control, vol. 42, No. 3 (May 1995), pages 429-442.

It consists in using, for each emission, not one transducer but a plurality of adjacent transducers. A delay law is applied to the adjacent emission transducers used so that they transmit, in the medium, a spherical ultrasound wave, close to that emitted by a single virtual source located at a certain distance from the sensor. The ultrasound wave thus emitted by the virtual source is more intense since its energy is proportional to the square root of the number of emission transducers forming said source. The SNR is improved, assuming that the noise generated is primarily electronic white noise. The principle also makes it possible to reduce structural noise, but to a lesser extent.

However, in the case of inspected parts generating significant structural noise on the signals, the improvement in the quality of the images eventually obtained by synthetic all-point focusing is more limited, the increase in the SNR is lower and the impact on detection is not as positive as might be hoped. This solution compensates in part for the above-mentioned problem, but does not eliminate it. Moreover, emitting by means of virtual sources does not make it possible to overcome the problem presented by reconstruction artifacts essentially due to parasitic echoes such as geometry echoes reflected by the interfaces of the part (edges, surface or bottom) or complex echoes including multiple reflections on the object and conversions of modes between the longitudinal waves and the transverse waves on each interaction with the object or an interface of the part. However, these artifacts may mask the real echo of a defect or be a false alarm. Moreover, this solution complicates the mode of acquisition and the reconstruction algorithms.

Another major disadvantage of the image reconstruction techniques as developed in the above-mentioned articles is the number of successive ultrasound firings required and the number of measurement ultrasound signals to be processed. This type of technique therefore is not suitable for real-time high-speed applications, in particular when the number of probe transducers is high.

According to a second family of acquisition techniques, an alternative to the ultrasound acquisition principle described above consists in successively emitting ultrasound plane waves having different emission angles by simultaneously exciting, each time, all of the emission transducers by means of suitable delay laws and receiving the echoes of said successive emissions with all of the N reception transducers. This alternative, generally qualified as "plane-wave compounding", is, for example, described in the article of G. Montaldo et al, entitled "Coherent plane-wave compounding for very high frame rate ultrasonography and transient elastography", published in IEEE Transactions on Ultrasonics Ferroelectrics and Frequency Control, vol. 56, No. 3, pages 489-506, March 2009.

This invention relates more specifically to this alternative, i.e. a processing method acquiring the ultrasound signals as follows:
- control of an array of M emission transducers for L successive ultrasound plane-wave emissions having L different successive emission angles in L emission zones,
- control of an array of N reception transducers so as to receive, simultaneously and for a predetermined duration, for each emission, N measurement time signals, measuring in particular echoes due to reflections of the emission considered,
- reconstitution of an imaged zone by calculating, at each point of a plurality of predetermined points of said imaged zone, a value resulting from a processing of at least some of the L×N measurement time signals received.

This second family of acquisition techniques is essentially envisaged in the medical field and implemented in certain high-speed echographs enabling maps of the elasticity of the human body to be imaged. The resulting image is high quality and requires only several dozen ultrasound firings (generally L is between 10 and 30) for a sensor of N=128 emission/reception transducers, by comparison with around 128 firings for the techniques of the first family. In addition, the resulting algorithms and the associated applications are particularly suitable for parallelization of calculations on GPU processors (Graphic Processing Unit) implemented in computer graphics cards. The performance of an echograph implementing a "plane-wave compounding" technique may thus, in practice, reach 10,000 images/s. Another advantage of this second family of acquisition techniques lies in the fact that each firing is performed by using all of the emission transducers so that the energy emitted is clearly higher, making this method less sensitive to attenuation, electronic or structural noise phenomena.

According to this second family of acquisition techniques and as taught in the article of G. Montaldo et al cited above, the processing of L×N measurement time signals received in order to construct an image is performed line by line (a line being defined as a straight line extending perpendicularly to the emission transducer array) by applying reception delay laws applied each time to only a small portion of the reception transducers, according to a well-known technique of "beamforming" or "dynamic depth focusing" (DDF). This makes it possible to obtain an image only in the opening of the sensor, said opening being defined by the distance between the first and last transducers. The sensor used must therefore have a large number of transducers because the size of the image obtained will be dependent upon it.

Generally, "plane-wave compounding" techniques are suitable for the medical field because, usually, the applications concerned consist in producing an image centered below the sensor, assuming that the medium is homogeneous. There are few if any refraction phenomena at the passage of the interface of the inspection medium, i.e. there is little acoustic contrast between the human/animal tissue and the coupling gel, or water if the body is placed in local immersion. There is also only one type of wave to be taken into account in the imaging, longitudinal or compression waves. In addition, the medium to be probed is assumed to be semi-infinite in most medical applications. All of this largely explains the spectacular imaging speeds of echographs because the algorithms are simplified.

However, in a non-destructive testing, these techniques do not provide satisfactory results. Indeed, in this field of application, the echoes may come from longitudinal waves (identified by the letter L) or transverse waves (identified by the letter T) capable also of including L↔T conversions between said two wave types during an interaction with a defect or an interface of the part. The inspection medium may be heterogeneous or anisotropic, for example in the case of large-grain steel, welds or composite materials. In addition, the interfaces of the inspection medium (i.e. the bottom, the surface and the edges of parts capable of forming often complex, for example water/steel, interfaces) must be capable of being taken into account with the resulting refraction and reflection phenomena. In addition, it is often sought to obtain an image that is not necessarily centered below a sensor but that extends laterally beyond the opening of the sensor. Finally, the most significant differentiation with respect to the medical field concerns the characteristics of the entities to be imaged. In a non-destructive testing, these characteristics are, for example, crack-type defects. They are generally elongate objects, located near an interface of the part and oriented perpendicularly to said interface (in general, it is the surface or bottom of a part). For this type of defect, the approach is very different from that of the medical field since it is advantageous to use reflection on an interface of the part in order to optimize the imaging. Based on current knowledge, the above-mentioned "plane-wave compounding" techniques are not suitable for imaging of this type of defect.

It may thus be desirable to provide an ultrasound signal processing method that makes it possible to overcome at least some of the problems and constraints mentioned above, while benefiting from the advantageous acquisition of signals by successive plane-wave emissions.

A method is therefore proposed for processing signals from an ultrasound probe acquisition including the following steps:
control of an array of M emission transducers for L successive emissions of ultrasound plane waves having L different successive emission angles in L emission zones,
control of an array of N reception transducers so as to simultaneously receive, for a predetermined duration, for each emission, N measurement time signals, measuring, in particular, echoes due to reflections of the emission considered,
reconstitution of an imaged zone by calculating, at each point of a plurality of predetermined points of said imaged zone, a value resulting from a processing of at least some of the L×N measurement time signals received,
wherein the reconstitution of the imaged zone includes the following steps, performed by a processor for each point of the imaged zone:
determination of L' emissions, L'≤L, among the L successive emissions, of which the emission zones include the point considered,
calculation of L'×N flight times, each flight time tl,n being the time taken for the l-th plane wave, the emission zone of which includes the point considered, where 1≤l≤L', to be received by the n-th reception transducer, where 1≤n≤N, passing through the point considered according to a predetermined propagation mode, and
coherent summing of L'×N instantaneous values taken respectively, by the L'×N measurement time signals received corresponding to the L' emissions determined, at the L'×N flight times calculated.

Thus, in so doing, the method proposed performs a "plane-wave compounding" acquisition without "beamforming" at the reception. It refers to the principle of synthetic focusing of the FMC acquisitions, but without being applied as such to "plane-wave compounding". This principle is, on the contrary, astutely adapted so as to both take advantage of the simplicity of the "plane-wave compounding" technique in order to obtain a high acquisition rate and image quality, in terms of spatial resolution and contrast, associated with synthetic all-point focusing of the image desired. It also makes it possible, owing to this synthetic all-point focusing, to obtain an image capable of extending beyond the opening of a sensor implementing it. Finally, the use of synthetic all-point focusing renders the method compatible with crack-type defect imaging, using the reflections of waves at the interface of the part examined, as is taught in document A. Fidahoussen et al cited above.

Optionally, the emission transducers are controlled by means of a delay law defined for each of the successive L emissions of ultrasound plane waves, each delay law making it possible to generate an ultrasound plane wave at a desired emission angle among the L different successive emission angles.

Also optionally, M=N and the transducers are sequentially emitters and receivers.

Also optionally, the L different successive emission angles are defined around a mean direction not perpendicular to the emission transducer array.

Also optionally, for each emission, i.e. for each emission angle, the predetermined mode of propagation is chosen from one of the following modes:
a direct-path propagation mode, with or without Longitudinal↔Transversal mode conversion, according to which the plane wave emitted is received directly by each point of the imaged zone and directly returned to the reception transducers without any other reflection,
a corner echo propagation mode, with or without Longitudinal↔Transversal mode conversions, according to which the wave emitted is subject to a reflection on a predetermined surface of the imaged zone, either between the emission transducers and each point of the imaged zone or between each point of the imaged zone and the reception transducers, and
an indirect-path propagation mode, with or without Longitudinal↔Transversal mode conversion, according to which the wave emitted is subject to at least two reflections against at least one predetermined surface of the imaged zone, at least once between the emission transducers and each point of the imaged zone and one other time between each point of the imaged zone and the reception transducers.

Also optionally, the imaged zone is included in the union of the L emission zones, its reconstitution including the following successive steps:
resetting of each point of the imaged zone to a zero value,
for any value of an index l ranging from 1 to L and for each point located in the intersection of the imaged zone and the l-th emission zone:
calculation of the N flight times tl,n,
coherent summing of the N instantaneous values taken, respectively, by the N measurement time signals received in response to the l-th emission, at the N calculated flight times, and
addition of the result of said coherent summing to the value of the point considered,
calculation of the modulus of the value finally obtained at each point of the imaged zone.

Also optionally, for each emission, an apodization of the M ultrasound signals emitted by the M emission transducers in order to form an ultrasound plane wave is performed by means of an apodization window such as a trapezoidal, Hamming or Blackman-Harris amplitude law.

Also optionally, the imaged zone takes the form of a sectorial zone delimited by the ends of the emission zones of maximum and minimum angles.

A computer program downloadable from a communication network and/or recorded on a computer-readable medium and/or capable of being run by a processor is also proposed, including instructions for executing the steps of an ultrasound signal processing method according to the invention, when said program is run on a computer.

An ultrasound probe device is also proposed, including:
a probe including M ultrasound emission transducers and N ultrasound reception transducers,
means for controlling the M emission transducers for L successive emissions of ultrasound plane waves having L different successive emission angles in L emission zones,
means for controlling the N reception transducers so as to simultaneously receive, for a predetermined period, for each emission, N measurement time signals, measuring, in particular, echoes due to reflections of the emission considered, and a processor for reconstituting an imaged zone by calculating, at each point of a plurality of predetermined points of said imaged zone, a value resulting from a processing of at least some of the L×N measurement time signals received, wherein the processor is further configured to perform the following processing operations for each point of the imaged zone:

determination of L' emissions, L'≤L, among the L successive emissions, of which the emission zones include the point considered, calculation of L'×N flight times, each flight time tl,n being the time taken for the l-th plane wave, the emission zone of which includes the point considered, where 1≤l≤L', to be received by the n-th reception transducer, where 1≤n≤N, passing through the point considered according to a predetermined propagation mode, and coherent summing of L'×N instantaneous values taken, respectively, by the L'×N measurement time signals received corresponding to the L' emissions determined, at the L'×N flight times calculated.

Figure 2:
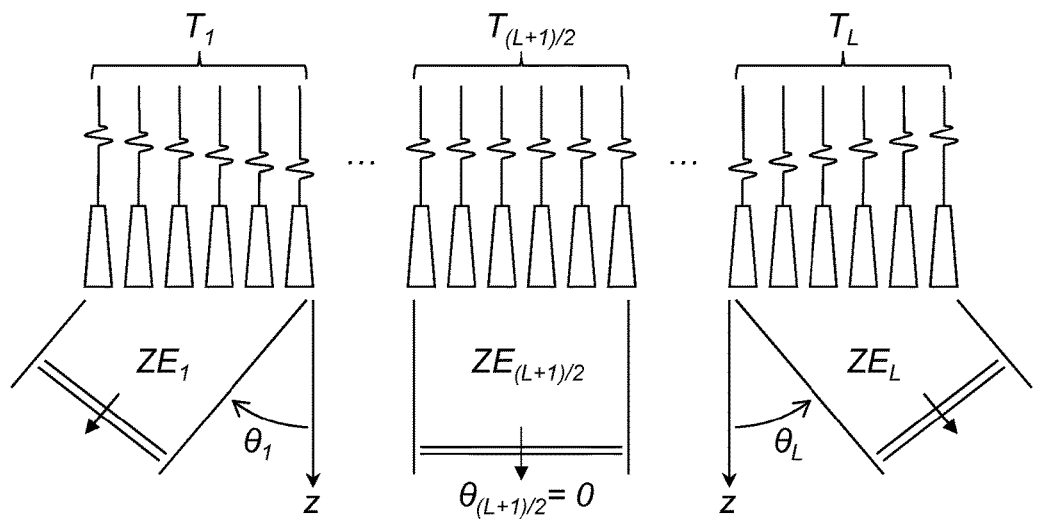
Figure 4:
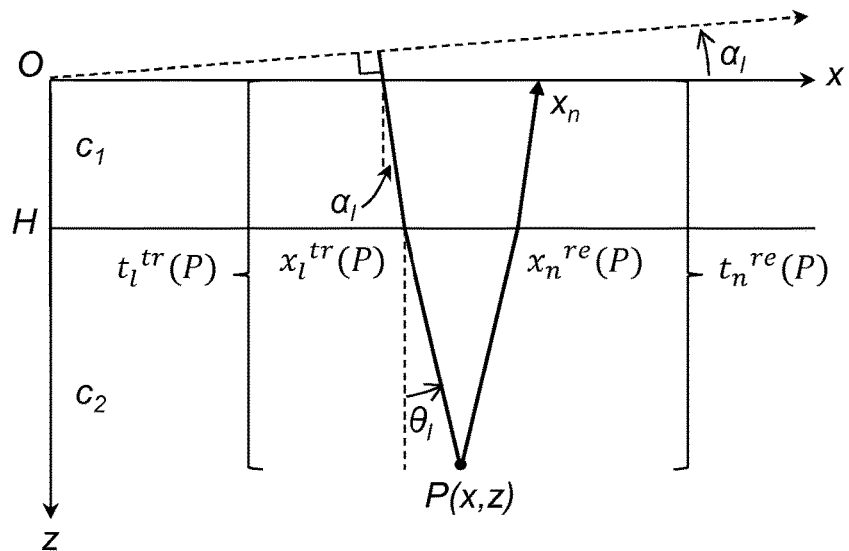
Figure 5:
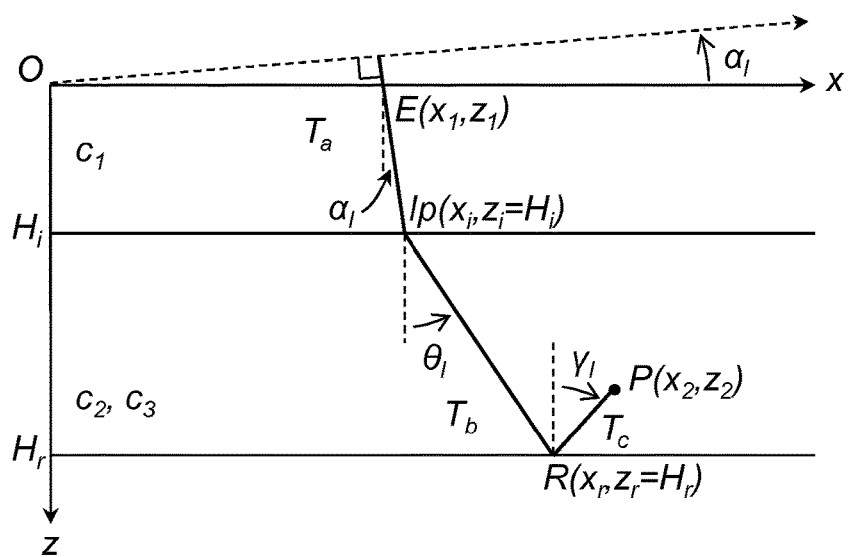
Figure 6:
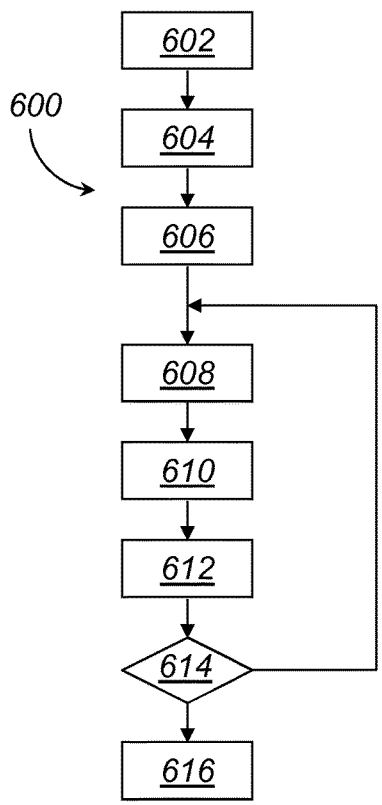
Figure 7:
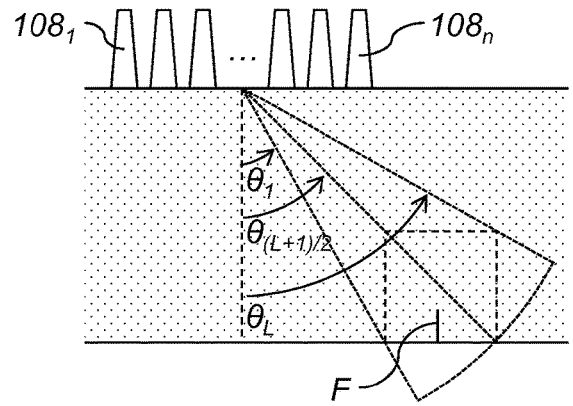
Figure 8:
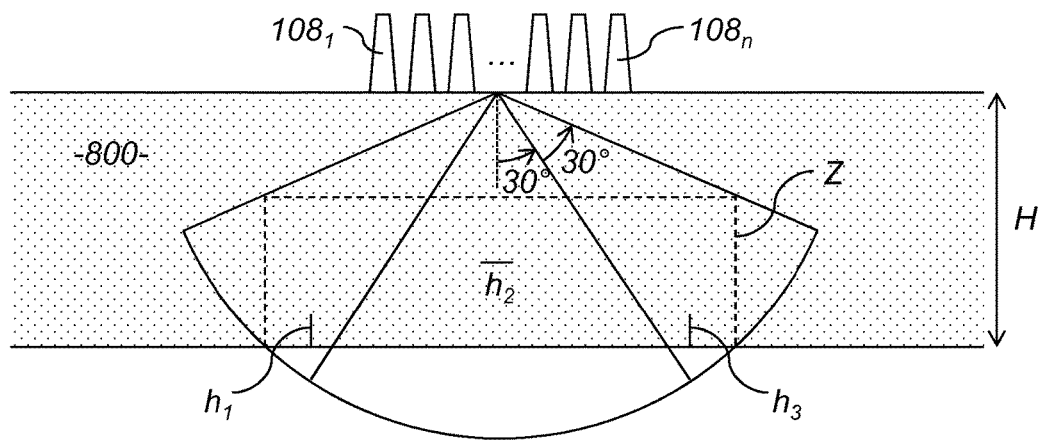
Figure 9:
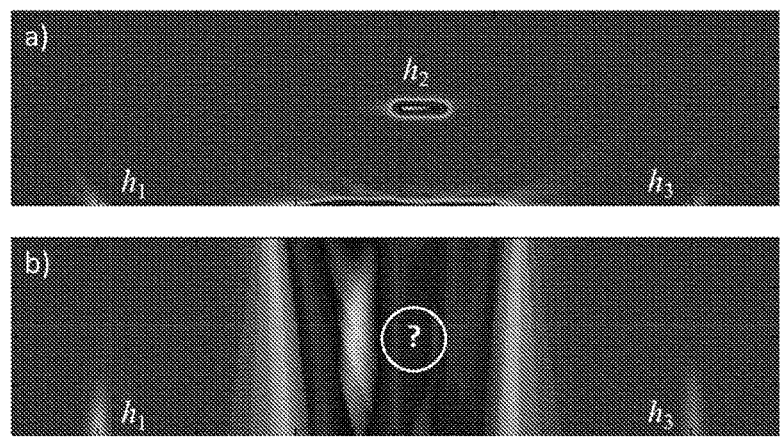
Figure 10:
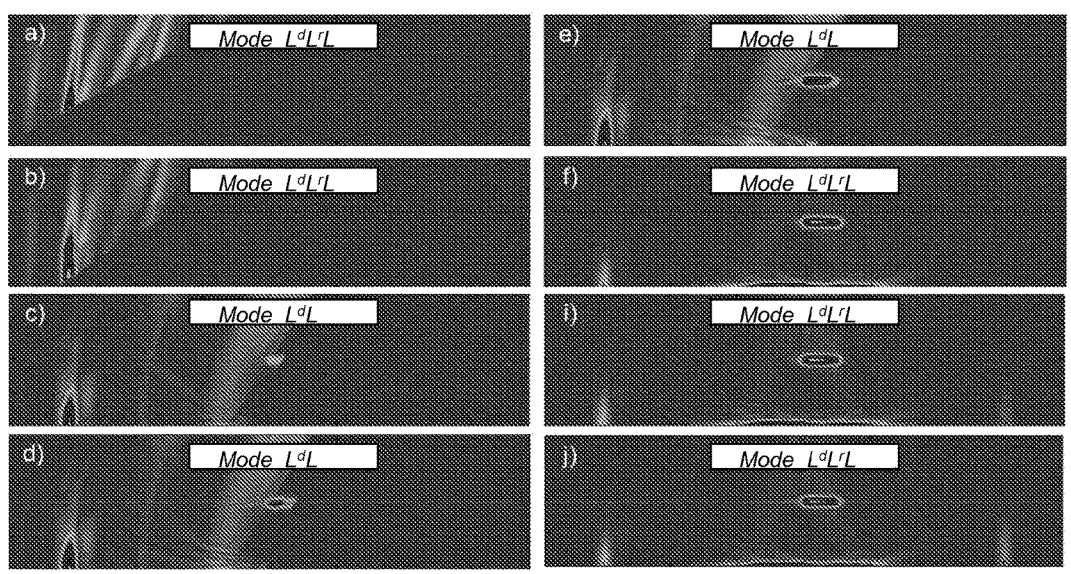

The invention will be easier to understand in view of the following description provided solely as an example, and with reference to the appended drawings, wherein:

FIG. 1 schematically shows the general structure of an ultrasound probe device according to an embodiment of the invention, FIG. 2 shows a principle of successive emissions of ultrasound plane waves implemented by the device of FIG. 1, FIGS. 3, 4 and 5 geometrically illustrate flight time calculations performed in the reconstitution of an imaged zone by the device of FIG. 1 when it implements the principle of FIG. 2, FIG. 6 shows the successive steps of a method for acquisition and processing of ultrasound signals implemented by the device of FIG. 1, according to an embodiment of the invention, FIG. 7 shows a first possible application of the method of FIG. 6, FIG. 8 shows a second possible application of the method of FIG. 6, and FIGS. 9 and 10 show different possible results of the application of FIG. 8.

In reference to FIG. 1, a probe device 100 of an object 102 according to an embodiment of the invention has an ultrasound probe 104 having a housing 106, i.e. a non-deformable structural element that serves as a reference attached to the probe 104, wherein an array of N fixed or mobile transducers $108_1, \ldots, 108_N$ are arranged, for example linearly or matricially.

The object 102 is, for example, a mechanical part to be examined by non-destructive testing or, in a medical context, a human or animal body part to be examined non-invasively. In the embodiment of FIG. 1, the object 102 is immersed in a liquid, such as water 110, and the probe 104 is held at a distance from the object 102 so that the water 110 separates them. However, in another equivalent embodiment, the probe 104 may be in direct contact with the object 102.

The transducers $108_1, \ldots, 108_N$ are designed so as to individually emit ultrasound waves toward the object 102 in response to control signals identified under general reference C, according to main directions parallel to one another, indicated by dotted-line arrows in FIG. 1, and in the main plane of the figure.

The transducers $108_1, \ldots, 108_N$ are further designed to detect echoes of ultrasound waves reflected on and in the object 102 and to provide measurement signals identified by general reference S and corresponding to said echoes. Thus, in the non-limiting example of FIG. 1, the transducers $108_1, \ldots, 108_N$ satisfy both the functions of emission and reception, but receivers different from the emitters may also be provided in different independent housings while remaining consistent with the principles of the invention.

The probe device 100 further has an electronic circuit 112 for controlling the transducers $108_1, \ldots, 108_N$ of the probe 104 and for processing the measurement signals S. This electronic circuit 112 is connected to the probe 104 so as to transmit the control signals C thereto and so as to receive the measurement signals S. The electronic circuit 112 is, for example, that of a computer. It has a central processing unit 114, such as a microprocessor designed to emit, to the probe 104, the control signals C and to receive, from the probe 104, the measurement signals S, and a memory 116 wherein in particular a computer program 118 is stored.

The computer program 118 first has instructions 120 for generating the signals C for controlling the transducers $108_1, \ldots, 108_N$ and receiving their echoes. These instructions are more specifically programmed so as to:

activate the transducers $108_1, \ldots, 108_N$ as emitters for L successive emissions of ultrasound plane waves having L different successive emission angles in L emission zones of the object 102, activate the transducers $108_1, \ldots, 108_N$ as receivers so as, after each emission, to simultaneously receive, by said N receivers and for a predetermined duration, of the desired inspection depth, N measurement time signals, measuring in particular echoes due to reflections of each emission considered.

The ultrasound plane waves are obtained upon emission by applying, to the transducers $108_1, \ldots, 108_N$ delay laws recorded in the memory 116 in a delay law base 122. Each delay law defines delays to be applied to the transducers $108_1, \ldots, 108_N$ in emission, so as to generate an ultrasound plane wave at a desired angle of emission among the L different successive emission angles. Therefore, there are as many delay laws as there are desired successive emissions.

Upon reception, the set S of the L×N measurement time signals received by the transducers $108_1, \ldots, 108_N$ is returned by the probe 104 to the central processing unit 114.

The computer program 118 further comprises instructions 124 for recording said signals, wherein $K_{l,n}(t)$ represents the measurement time signal received by the transducer $108_n$ in response to the l-th ultrasound plane-wave emission.

The computer program 118 further comprises instructions 126 for reconstituting an imaged zone by calculating, at each point of a plurality of predetermined points of said imaged zone, a value resulting from a processing of at least some of the L×N measurement time signals received. More specifically, as the imaged zone is, for example, defined as being a digital image consisting of pixels, the instructions 126 are defined for, at each pixel of said image:

determining L' emissions, L'≤L, among the L successive emissions, of which the emission zones include the pixel considered, calculating L'×N flight times, each flight time $t_{l,n}$ being the time taken for the l-th plane wave of which the emission zone includes the pixel considered, where 1≤l≤L', to be received by the n-th reception transducer, where 1≤n≤N, passing through the pixel considered according to a predetermined propagation mode, coherently summing the L'×N instantaneous values taken, respectively, by the L'×N measurement time signals received corresponding to the L' emissions determined, at the L'×N flight times calculated, and calculating the modulus of the value obtained optionally weighted by the value L'.

Finally, the computer program 118 comprises instructions 128 for displaying the digital image obtained on a display device, not shown.

As illustrated in FIG. 2, in a case where the number L of successive emissions is odd and where the angles of emission are followed with a constant step in a symmetrical angular sector with respect to the direction z orthogonal to the transducer array $108_1, \ldots, 108_N$, the first plane wave emission is associated with a delay law $T_1$ concerning pulses emitted by the transducers $108_1, \ldots, 108_N$, enabling the emission of a plane wave having an angle of emission $\theta_1$ with respect to the direction z in a first emission zone $ZE_1$ located partially outside the opening of the probe 104. The (L+1)/2-th plane wave emission is associated with a uniform delay law $T_{(L+1)/2}$ for the emission of a plane wave having a zero angle of emission with respect to the direction z in a (L+1)/2-th emission zone $ZE_{(L+1)/2}$ covering the opening of the probe 104. Finally, the last plane wave emission is associated with a delay law $T_L$ enabling the emission of a plane wave having an angle of emission $\theta_L = -\theta_1$ with respect to the direction z in a last emission zone $ZE_L$ located partially outside of the opening of the probe 104. In general, the l-th plane wave emission is associated with a delay law $T_l$ enabling the emission of a plane wave having an angle of emission $\theta_l = \theta_1 + (l-1) \cdot (\theta_L - \theta_1)/(L-1)$ with respect to direction z.

To improve the quality of the measurement signals used to reconstruct the imaged zone, it is also possible to apply an apodization of the ultrasound signals emitted by the transducers $108_1, \ldots, 108_N$ so as to form an ultrasound plane wave of higher quality, without distortion due to edge effects. Such an apodization is performed at each emission spatially on all of the transducers by means of an apodization window such as a trapezoidal, Hamming or Blackman-Harris amplitude law. It has the effect of providing a better definition of the successive emission zones.

In consideration of the acquisition technique used, the zone to be imaged must be contained in the union of the L successive emission zones. The result is that said zone may extend beyond the opening of the probe 104 as can be seen in FIG. 2. In particular, the imaged zone may take the form of a sectorial zone delimited by the ends of emission zones of maximum and minimum angles. An S-scan image may thus be obtained.

Figure 3:
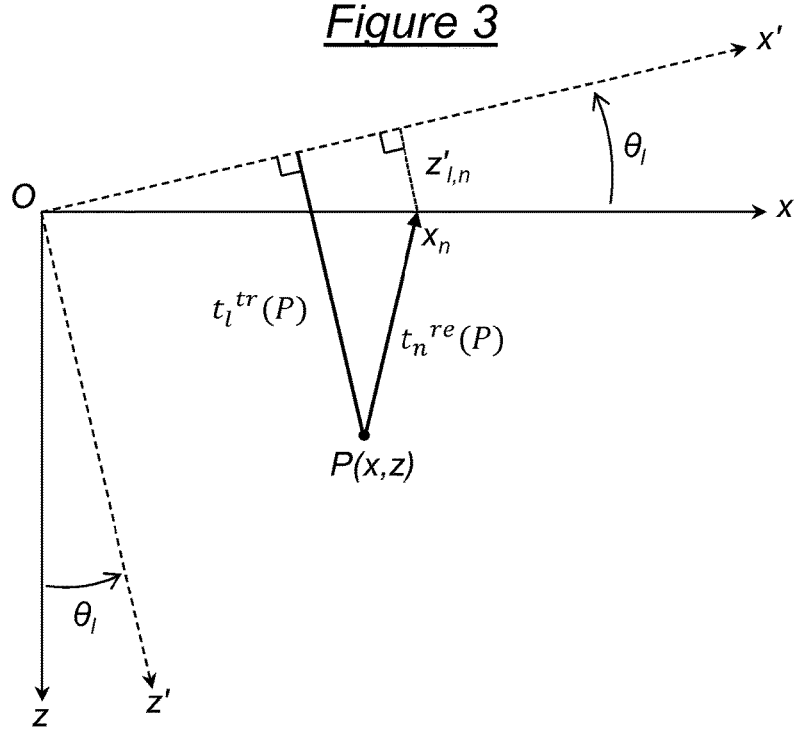

In reference to FIG. 3 showing a 2D application of the invention, for the l-th ultrasound plane wave emission of emission angle $\theta_l$, the direct-path flight time $t_{l,n}(P)$ relative to a point P of coordinates (x, z) in the reference system (O, x, z) associated with the plane of the zone to be imaged where the axis (O, x) is the axis of the transducer array $108_1, \ldots, 108_N$, and relative to transducer $108_n$ the coordinates of which are $(x_n, 0)$ in the same reference system (O, x, z), is broken down as follows:

$$t_{l,n}(P) = t_l^{tr}(P) + t_n^{re}(P)$$

where $t_l^{tr}(P)$ is the emission flight time between the plane (O, x') of emission of the plane wave and point P and $t_n^{re}(P)$ is the reception flight time between the point P and the transducer $108_n$.

By a geometric calculation, the emission flight time is expressed as follows:

$$t_l^{tr}(P) = \frac{x \cdot \sin(\theta_l) + z \cdot \cos(\theta_l)}{c}$$

where c is the speed of propagation of the plane wave in the medium considered (assuming that there is no change in medium, which is verified in cases of non-destructive testing on contact). It is noted that said emission flight time for point P is not dependent upon transducers $108_1, \ldots, 108_N$, but only upon the emission angle $\theta_l$.

By a geometric calculation as well, the reception flight time is expressed as follows:

$$t_n^{re}(P) = \frac{\sqrt{(x_n - x)^2 + z^2}}{c}$$

where it is noted that said reception flight time for point P is dependent only upon transducers $108_1, \ldots, 108_N$, but not upon the emission angle $\theta_l$.

The total flight time is therefore expressed as follows:

$$t_{l,n}(P) = \frac{x \cdot \sin(\theta_l) + z \cdot \cos(\theta_l)}{c} + \frac{\sqrt{(x_n - x)^2 + z^2}}{c}$$

To coherently sum L'×N instantaneous values taken, respectively, by L'×N measurement time signals received corresponding to L' emissions determined contributing to the zone imaged at point P, at the L'×N flight times as calculated above, it is also appropriate, in practice, for the sake of time recalibration, to apply a constant $\tau_l^{tr}$ specific to each emission, the value of which is expressed as follows:

$$\tau_l^{tr} = \frac{\max_n(z'_{l,n})}{2 \cdot c}$$

where $z'_{l,n}$ represents the distance between the transducer $108_n$ and the axis of the transducer array (O, x') virtually angularly shifted from the axis (O, x) by an angle equal to $\theta_l$. This distance may be calculated according to the following formula:

$$z'_{l,n} = x_n \cdot \sin(\theta_l) - \min_n[x_n \cdot \sin(\theta_l)]$$

The above calculation, and in particular the value $\min_n[x_n \cdot \sin(\theta_l)]$, ensures that the delays applied in the delay laws always remain positive, even when the angle $\theta_l$ is negative. Moreover, in the case of an inspected part with a planar surface, the constant $\tau_l^{tr}$ specific to each emission corresponds to the mean delay of the delay law applied to the l-th emission, or, equivalently, to half of the maximum delay.

The result is that the modulus of the coherent summing defined above, involving the L'×N measurement time signals contributing to the zone imaged at point P, may be expressed as follows:

$$A(P) = |\Sigma_{l=1}^{L'} \Sigma_{n=1}^{N} K_{l,n}[t_{l,n}(P) + \tau_l^{tr}]|$$

In practice, to obtain the image envelope, it is instead the analytical signals that are summed, in particular by means of Hilbert $H_{l,n}(t)$ of the signals $K_{l,n}(t)$. The above calculation then becomes, more specifically:

$$A_{env}(P) = |\Sigma_{l=1}^L \Sigma_{n=1}^N (K_{l,n}[t_{l,n}(P) + \tau_l^{tr}] + H_{l,n}[t_{l,n}(P) + \tau_l^{tr}])|$$

It is noted that, in accordance with said calculation close to an all-point focusing, no delay law is applied on reception.

The advantage of reconstituting the zone to be imaged by such a technique based on flight time calculations at each point is that it is possible to take into account different configurations and modes of propagation of the ultrasound waves. Thus, for example, in the previous calculations, it was considered, for the sake of simplicity, that the mode of propagation of the ultrasound waves was direct, without changing the propagation medium (probe in contact with the object to be inspected) and without polarization conversion of the waves emitted, i.e. each plane wave emitted is received directly by each point of the imaged zone and returned directly to the transducers $108_1, \ldots, 108_N$ without other reflection.

However, other hypotheses may be made and it would then be sufficient to adapt the flight time calculation:
- the examination of the object considered may be performed with immersion without contact, with a more or less complex object surface,
- the mode of propagation of the ultrasound waves may be a corner echo mode, in particular in the vicinity of a crack-type defect and according to a certain plane wave incidence: in this case, the plane wave emitted is subject to a reflection against a predetermined surface of the imaged zone, for example the bottom of the object, either between the transducers $108_1, \ldots, 108_N$ and each point of the imaged zone, or between each point of the imaged zone and the transducers $108_1, \ldots, 108_N$,
- the mode of propagation of the ultrasound waves may be an indirect-path mode, in particular also in the vicinity of a crack-type defect and according to a certain plane wave incidence: in this case, the plane wave emitted is subject to at least two reflections against at least one predetermined surface of the imaged zone, for example the bottom of the object, at least once between the transducers $108_1, \ldots, 108_N$ and each point of the imaged zone and another time between each point of the imaged zone and the transducers $108_1, \ldots, 108_N$,
- regardless of the propagation mode, the longitudinal or transverse polarization of the ultrasound waves may vary upon a reflection: a transverse wave may become longitudinal and vice versa, said conversion having an impact on the propagation speed.

The above hypotheses may also be combined.

As an example, FIG. 4 shows an examination with immersion without contact according to which the propagation is performed, in direct mode, in a first medium at speed $c_1$, for example water, then in a second medium at speed $c_2$, for example the material (steel, . . . ) of the object inspected. The two media are, in this particular case, delimited by the planar surface of the object located at a distance H from the axis (O, x) of the transducer array $108_1, \ldots, 108_N$.

Using the notations of FIG. 3 and adding those of FIG. 4, the calculation of points of impact $x_l^{tr}(P)$ and $x_n^{re}(P)$ on the planar surface of the object should be taken into account in order to calculate the total flight time $t_{l,n}(P)$.

By emitting a plane wave in the first medium, above the planar surface of the object, with an angle of incidence $\alpha_l$, it is possible to deduce the angle of incidence $\theta_l$ of the plane wave in the second medium under the surface of the object by the Snell-Descartes law, written as follows:

$$\theta_l = \sin^{-1}\left(\frac{c_2}{c_1}\sin(\alpha_l)\right)$$

Then, knowing the coordinates x and z of the focusing point P in the object inspected, the abscissa $x_l^{tr}(P)$ of the point of impact on the surface associated with the emission path is deduced:

$$x_l^{tr}(P) = x - (z - H) \cdot \tan(\theta_l)$$

Then, the emission flight time to point P is written:

$$t_l^{tr}(P) = \frac{\sqrt{H^2 + [x_l^{tr}(P)]^2}}{c_1} + \frac{(x - x_l^{tr}(P))\sin\theta_l + (z - H)\cos\theta_l}{c_2}$$

As above, it is noted that said emission flight time for point P is not dependent upon transducers $108_1, \ldots, 108_N$, but only the angle of emission $\theta_l$.

In reception, similarly:

$$t_n^{re}(P) = \frac{\sqrt{H^2 + [x_n^{re}(P)]^2}}{c_1} + \frac{\sqrt{(x_n^{re}(P) - x)^2 + (z - H)^2}}{c_2}$$

where the abscissa $x_n^{re}(P)$ of the point of impact in reception is determined on the basis of Fermat's principle according to which the return path between point P and the receiver $108_n$ must correspond to the shortest path. In the case of a planar part, the principle involves the search for zeroes of a function. The methods generally used to solve such a zero search are diverse: The Newton-Raphson method, the Ferrari method, the Laguerre method, the gradient descent method, and so on. The Newton-Raphson and gradient descent methods are the more beneficial because they remain valid for complex surface geometries. There are in particular numerous prior art documents on the search for shorter paths and on the calculation of points of impact. These methods therefore will not be mentioned.

As above, it is demonstrated that the reception flight time for point P is dependent only on transducers $108_1, \ldots, 108_N$, but not on the angle of incidence $\theta_l$.

As an additional example, FIG. 5 shows an examination with immersion without contact according to which the propagation is performed, in corner echo mode, in a first medium at speed $c_1$, for example water, then in a second medium, for example the material (steel, etc.) of the object inspected. In the second medium, the propagation is performed at speed $c_2$ for the longitudinal waves and at speed $c_3$ for transverse waves. The two media are, in this particular case, delimited by the planar surface of the object located at a distance $H_i$ from the axis (O, x) of the transducer array $108_1, \ldots, 108_N$. The object also has a planar bottom, at a distance $H_r$ from the axis (O, x), against which a planar incident wave is reflected according to the corner echo propagation principle. Only the incident path at point P is shown, the return path being similar to that of the previous example.

The incident path of the l-th planar wave emission is thus broken down into three parts:
- a first part $T_a$ between its theoretical emission point E of coordinates $(x_1, z_1)$ on the axis (O, x) and a point of impact Ip of coordinates $(x_i, z_i=H_i)$ at the interface of the two media, oriented according to an angle $\alpha_l$ with respect to the direction $(O, z)$, a second part $T_b$ between the point of impact Ip and a reflection point R of coordinates $(x_r, z_r=H_r)$ at the bottom of the object, oriented according to angle $\theta_l$ with respect to the direction $(O, z)$, and a third part $T_c$ between the point of reflection R and the point P of coordinates denoted $(x_2, z_2)$, oriented according to an angle $\gamma_l$ with respect to the direction $(O, z)$.

It is also assumed that the wave is longitudinal on paths $T_a$ and $T_b$, then transversal on the path $T_c$, a polarization conversion occurring upon the reflection against the bottom of the object.

In accordance with the Snell-Descartes law, the refraction principle must be verified at point Ip and the reflection principle must be verified at point R. This produces the following system of equations:

$$\begin{cases} \dfrac{\sin(\alpha_l)}{c_1} = \dfrac{\sin(\alpha_l)}{c_2} \\ \dfrac{\sin(\theta_l)}{c_2} = \dfrac{\sin(\gamma_l)}{c_3} \end{cases}$$

To pose the problem in Cartesian coordinates, the sines are expressed as a function of the coordinates of points E, Ip, R and P:

$$\sin(\alpha_l) = \frac{(x_i - x_1)}{\sqrt{(x_i - x_1)^2 + (H_i - z_1)^2}}$$

$$\sin(\theta_l) = \frac{(x_r - x_i)}{\sqrt{(x_r - x_i)^2 + (H_r - H_i)^2}}$$

$$\sin(\gamma_1) = \frac{(x_2 - x_r)}{\sqrt{(x_2 - x_r)^2 + (z_2 - H_r)^2}}$$

The system of equations above may then be expressed as follows:

$$\begin{cases} f_1 : c_2(x_i - x_1)\sqrt{(x_r - x_i)^2 + (H_r - H_i)^2} \; - \\ \quad c_1(x_r - x_i)\sqrt{(x_i - x_1)^2 + (H_i - z_1)^2} = 0 \\ f_2 : c_3(x_r - x_i)\sqrt{(x_2 - x_r)^2 + (z_2 - H_r)^2} \; - \\ \quad c_2(x_2 - x_r)\sqrt{(x_r - x_i)^2 + (H_r - H_i)^2} = 0 \end{cases}$$

This system of two nonlinear equations with two unknowns, $x_i$ and $x_r$, is classically solved by means of the Newton-Raphson method. It makes it possible to determine points Ip and R, then to deduce the emission flight time $t_l^{tr}(P)$.

In reference to FIG. 6, an example of an ultrasound signal acquisition and processing method 600 implemented by the device 100 of FIG. 1 will now be described according to a preferred embodiment of the invention.

In a step 602, the processing unit 114 carrying out the instructions 120 orders the sequences of emissions and receptions of transducers $108_1, \ldots, 108_N$ for the acquisition of measurement signals $K_{l,n}(t)$.

There are L of these sequences, L being an integer number capable of being much lower than the number N of transducers $108_1, \ldots, 108_N$. After each firing, the signals are received on the set of N transducers, digitized and transmitted to the electronic circuit 112.

In a step 604, the processing unit 114 carrying out the instructions 124 records the measurement signals $K_{l,n}(t)$, said signals being digitized so as to facilitate their subsequent processing. Steps 602 and 604 may be carried out simultaneously, i.e. it is unnecessary to wait for all of the firings to be performed in order to begin to record the measurement signals and reconstitute an image.

In a next step 606, the processing unit 114 carrying out the instructions 126 resets each pixel of the zone to be imaged, chosen in the union of the L emission zones, at a zero value. Moreover, an index I intended to vary from 1 to L is reset to 1. This step may be carried out independently of steps 602 and 604, before, during or after.

In the next step 608, for each pixel of the zone to be imaged located in the l-th emission zone, the N flight times $t_{l,n}$, $1 \leq n \leq N$, are calculated according to a propagation mode chosen specifically for the angle of emission $\theta_l$, according, for example, to one of the calculations presented above. It therefore appears that multiple propagation modes with or without polarization conversions may respectively be chosen for the L successive emissions. The invention therefore makes it possible to fuse multiple ultrasound reconstruction modes in a single zone to be imaged.

In a step 610, for each pixel of the zone to be imaged located in the l-th emission zone, the N instantaneous values taken, respectively, by the N measurement time signals received in response to the l-th emission, at the N flight times calculated above, are summed in accordance with the following coherent summing operation:

$$A_l(P) = \Sigma_{n=1}^N (K_{l,n}[t_{l,n}(P) + \tau_l^{tr}] + H_{l,n}[t_{l,n}(P) + \tau_l^{tr}])$$

where $A_l(P)$ is the amplitude of the pixel P for the l-th emission.

In a step 612, for each pixel of the zone to be imaged located in the l-th emission zone, the result of the coherent summing is added to the current value of the pixel considered and the index I is incremented by one unit.

Then, in a test step 614, if l is strictly lower than L, the method returns to step 608. Otherwise, it goes to a final step 616.

In the final step 616, the modulus of the value finally obtained at each point of the imaged zone is calculated, so that the value $A_{env}(P)$ defined above is obtained at each pixel P:

$$A_{env}(P) = |\Sigma_{l=1}^L A_l(P)|$$

A weighting of the pixel values by the number of firings having contributed to the value of each of them may optionally be performed, with the understanding that the pixels close to the mean angle of the emissions receive more ultrasound waves than those farther away.

Each loop of steps 608, 610 and 612 of the iterations on the index I may be carried out in parallel with steps 602 and 604 since the processing performed in each of said loops is dependent only upon the results of a single ultrasound firing. It is in particular unnecessary to wait for all of the firings to be performed in order to begin the calculations of the iterative process 608-610-612-614. Steps 608, 610, 612, 614 and 616 are, moreover, like step 606, carried out by the processing unit 114 by means of instructions 126.

In the last step 616 also, the processing unit 114 carrying out instructions 128 displays the resulting image.

Owing to the implementation of this preferred embodiment, the imaged zone may be progressively reconstructed, angle by angle, updating for each firing angle only the values of pixel located in the firing zone, the contours of said zone being better defined as an effective apodization has been performed on the emission of the ultrasound plane wave. It is therefore unnecessary to perform calculations for all of the pixels of the final image on each firing. This principle is particularly advantageous when the final image extends largely beyond the dimensions of the sensor.

As shown in FIG. 7, one of the advantages of the invention is also that the L different successive emission angles $\theta_1$ to $\theta_L$ may be defined around a mean direction $\theta_{(L+1)/2}$ not perpendicular to the transducer array $108_1, \ldots, 108_N$. In particular, when it involves detecting defects such as a crack F at the bottom of an object to be inspected in a non-destructive testing, said crack F also being perpendicular to the transducer array, it is preferable to laterally offset the zone to be inspected with respect to the probe 104 and to emit around a mean of 45° for example. Thus, the crack becomes more visible. It is also advantageously detected over its entire length by choosing a corner echo propagation mode in its vicinity with a possible polarization conversion, which is also possible in the implementation of the invention as seen above. The zone to be inspected may even be offset so as to completely leave the opening of the probe 104, which is not possible in conventional "beamforming" methods.

Another example of a concrete application of the method described above is shown in FIG. 8. This application was the subject of real tests, the various results of which will be discussed in reference to FIGS. 9 and 10.

The inspected part 800 is made of stainless steel and has three artificial notch-type defects. Two notches, $h_1$ and $h_3$, are oriented perpendicularly to the transducer array $108_1, \ldots, 108_n$ and located at the bottom of the inspected part 800 outside of the opening of the sensor formed by the set of transducers $108_1, \ldots, 108_n$. A third notch, $h_2$, has an orientation parallel to the transducer array $108_1, \ldots, 108_n$ and is located in the vicinity of the normal to the sensor that they form. The depth of the part is H=70 mm, the number N of transducers is equal to 64 (inter-transducer step of 0.6 mm, central frequency of the ultrasound waves emitted of 5 MHz), the inspected part is in contact with the transducers centered on the notch $h_2$. The three notches have a length of 10 mm.

Thirty-one successive ultrasound plane wave emissions with emission angles ranging from −60° to +60° (with respect to the normal of the sensor) per 4° step are carried out. Among these 31 successive emissions, the following are distinguished: a first group of emissions oriented around −45°, more specifically between −60° and −30°, this first group covering an angular sector wherein the notch $h_1$ is located; a second group of emissions oriented around the normal (0°), more generally between −30° and +30°, this second group covering an angular sector wherein the notch $h_2$ is located; and a third group of emissions oriented around +45°, more specifically between +30° and +60°, this third group covering an angular sector wherein the notch $h_3$ is located. The imaged zone is included in the union of the emission zones and is identified by reference Z.

According to a first possible reconstitution of the imaged zone Z, the same direct-path and longitudinal wave propagation mode is applied to the processing of measurement signals of all ultrasound firings. This mode is symbolized by the notation $L^dL$, where "L" indicates a rectilinear sub-path in longitudinal polarization and "$^d$" indicates a plane wave interaction with a defect. More generally, the direct-path propagation mode is symbolized by the notation $X^dX$, where "X" may take the value "L" or "T" (for a rectilinear sub-path in transversal polarization) on each sub-path. The reconstitution with the single mode $L^dL$ provides the result of FIG. 9(a). The notch $h_2$ is imaged in its entirety, while the two other notches $h_1$ and $h_3$ are characterized each by a single diffraction echo, located at the bottom of each defect. The diffraction echo of the top of the notches is in fact barely visible in the two cases.

According to a second possible reconstitution of the imaged zone Z, the same corner echo and longitudinal wave propagation mode is applied to the processing of measurement signals of all ultrasound firings. This mode is symbolized by the notation $L^dL'L$, where "'" indicates a plane wave interaction with the bottom of the inspected part. More generally, the corner echo propagation mode is symbolized by the notation $X^dX'X$, where "X" may take the value "L" or "T" on each sub-path. The reconstitution with the single mode $L^dL'L$ provides the result of FIG. 9(b). The notches $h_1$ and $h_3$ are this time clearly visible over their entire length, but the notch $h_2$ is completely masked by a reconstruction artifact. This artifact is explained by the presence of the bottom echo, which is a direct echo. More specifically, the artifact located in the opening of the sensor corresponds to the repositioning of the direct echo coming from the bottom of the part inspected at flight times corresponding to corner echo paths. There is a contradiction between the nature of the echo and the reconstruction mode.

According to a third possible reconstitution of the imaged zone Z, taking advantage of the two previous imperfect reconstitutions:
  a first mode of propagation $L^dL'L$ is applied to the processing of the measurement signals from the first group of emissions between −60° and −30°, this propagation mode being adapted to the configuration of notch $h_1$,
  a second mode of propagation $L^dL$ is applied to the processing of the measurement signals from the second group of emissions between −30° and +30°, this propagation mode being adapted to the configuration of notch $h_2$, and
  a third mode of propagation $L^dL'L$ is applied to the processing of the measurement signals from the third group of emissions between +30° and +60°, this propagation mode being adapted to the configuration of notch $h_3$.

This third reconstitution provides the progressive results of FIG. 10. FIG. 10(a) shows the intermediate result of the ultrasound firing n°1 (−60°), while the propagation mode chosen is $L^dL'L$. FIG. 10(b) shows the intermediate result of the ultrasound firing n°2 (−56°), while the propagation mode chosen is still $L^dL'L$. FIG. 10(c) shows the intermediate result of the ultrasound firing n°9 (−28°), while the propagation mode chosen is $L^dL$. FIG. 10(d) shows the intermediate result of the ultrasound firing n°10 (−24°), while the propagation mode chosen is still $L^dL$. FIG. 10(e) shows the intermediate result of the ultrasound firing n°11 (−20°), while the propagation mode chosen is still $L^dL$. FIG. 10(f) shows the intermediate result of the ultrasound firing n°24 (+32°), while the propagation mode chosen is again $L^dL'L$. FIG. 10(i) shows the intermediate result of the ultrasound firing n°26 (+40°), while the propagation mode chose in still $L^dL'L$. Finally, FIG. 10(j) shows the final result of the ultrasound firing n°31 (+60°), while the propagation mode chosen is still $L^dL'L$.

The image 10(*j*) is to be compared with images 9(*a*) and 9(*b*). The visibility of the three notches is clearly greater, owing to the possibility offered by a method according to the invention of adapting the propagation mode chosen during reconstitution as a function of the angle of emission of 5 successive ultrasound firings.

It clearly appears that a method and a device as described above make it possible to perform a smaller number of firings than that necessary in the all-point focusing methods for an equivalent image quality finally obtained or in order to achieve better performance in terms of image quality for an equivalent number of firings. The main reason for this improvement, i.e. higher speed or better image quality, is that, on each firing, all of the emission transducers are used.

In addition, the method proposed remains compatible with complex geometries or materials and makes it possible to fuse a plurality of propagation modes in the same image, according to the firing angle. Images extending beyond the opening of the sensor may also be obtained.

In the case of a progressive reconstitution of the image, angle by angle, as is made possible by the invention, the outcome is finally improved.

Finally, experimental tests show that the detection amplitude is clearly higher with a method according to the invention than with a classic all-point focusing method. In comparative studies, a factor of 10 between the two methods was demonstrated. The reason for this difference is again the use of all of the emission transducers in each firing.

It should also be noted that the invention is not limited to the embodiment described above. It will indeed appear to a person skilled in the art that various modifications may be made to the embodiment described above, in light of the teaching disclosed above.

In particular, the computer program instructions may be replaced by electronic circuits dedicated to functions performed during the execution of said instructions.

In general, in the claims below, the terms used must not be interpreted as limiting the claims to the embodiment described in the present description, but must be interpreted so as to include all of the equivalents that the claims are intended to cover owing to their wording, and which are available to a person skilled in the art applying general knowledge to the implementation of the teaching disclosed above.

The invention claimed is:

1. A method for processing signals from an ultrasound probe acquisition, the method comprising:
    controlling, via processing circuitry, of an array of M emission transducers for L successive emissions of ultrasound plane waves having L different successive emission angles in L emission zones;
    controlling, via the processing circuitry, of an array of N reception transducers so as to simultaneously receive for a predetermined duration, for each emission, N measurement time signals, measuring echoes due to reflections of the emission considered;
    reconstituting, via the processing circuitry, of an imaged zone by calculating, at each point of a plurality of predetermined points of the imaged zone, a value resulting from a processing of at least some of L×N measurement time signals received, wherein
    the reconstituting of the imaged zone includes the following, performed by the processing circuitry for each point of the imaged zone:
        determining of L' emissions, L'≤L, among the L successive emissions, of which the emission zones include the point considered,
        calculating of L'×N flight times, each flight time $t_{l,n}$ being time taken for an l-th plane wave, the emission zone of which includes the point considered, where 1≤l≤L', to be received by an n-th reception transducer, where 1≤n≤N, passing through the point considered according to a predetermined propagation mode,
        coherent summing of L'×N instantaneous values taken respectively, by the L'×N measurement time signals received corresponding to the L' emissions determined, at the L'×N flight times calculated; and
    generating and displaying the imaged zone on a display.

2. The method for processing signals according to claim 1, wherein the emission transducers are controlled by a delay law defined for each of the successive L emissions of ultrasound plane waves, each delay law enabling generation of an ultrasound plane wave at a desired emission angle among the L different successive emission angles.

3. The method for processing signals according to claim 1, wherein M=N and the transducers are sequentially emitters and receivers.

4. The method for processing signals according to claim 1, wherein the L different successive emission angles are defined around a mean direction (θ(L+1)/2) not perpendicular to the emission transducer array.

5. The method for processing signals according to claim 1, wherein, for each emission angle, the predetermined propagation mode is chosen from one of the following modes:
    a direct-path propagation mode, with or without Longitudina↔Transversal mode conversion, according to which the plane wave emitted is received directly by each point of the imaged zone and directly returned to the reception transducers without any other reflection,
    a corner echo propagation mode, with or without Longitudina↔Transversal mode conversions, according to which the wave emitted undergoes a reflection on a predetermined surface of the imaged zone, either between the emission transducers and each point of the imaged zone or between each point of the imaged zone and the reception transducers, and
    an indirect-path propagation mode, with or without Longitudinal↔Transversal mode conversion, according to which the wave emitted undergoes at least two reflections against at least one predetermined surface of the imaged zone, at least once between the emission transducers and each point of the imaged zone and one other time between each point of the imaged zone and the reception transducers.

6. The method for processing signals according to claim 1, wherein the imaged zone is included in a union of the L emission zones, the reconstitution of the imaged zone including a following:
    resetting of each point of the imaged zone at a zero value,
    for any value of an index I ranging from 1 to L and for each point located in the intersection of the imaged zone and an I-th emission zone:
        calculating of the N flight times $t_{l,n}$,
        coherent summing of the N instantaneous values taken, respectively, by the N measurement time signals received in response to the I-th emission, at the N calculated flight times,
        adding of the result of said coherent summing to the value of the point considered, and
    calculating of a modulus of a value finally obtained at each point of the imaged zone.

7. The method for processing signals according to claim 1, wherein, for each emission, an apodization of the M ultrasound signals emitted by the M emission transducers in order to form an ultrasound plane wave is performed by an apodization window such as a trapezoidal, Hamming or Blackman-Harris amplitude law.

8. The method for processing signals according to claim 1, wherein the imaged zone takes the form of a sectorial zone delimited by the ends of the emission zones of maximum and minimum angles.

9. A non-transitory computer-readable storage medium including computer executable instructions, wherein the instructions, when executed by a computer, cause the computer to perform:

controlling of an array of M emission transducers for L successive emissions of ultrasound plane waves having L different successive emission angles in L emission zones;

controlling of an array of N reception transducers so as to simultaneously receive for a predetermined duration, for each emission, N measurement time signals, measuring echoes due to reflections of the emission considered;

reconstituting of an imaged zone by calculating, at each point of a plurality of predetermined points of the imaged zone, a value resulting from a processing of at least some of L×N measurement time signals received, wherein the reconstituting of the imaged zone includes the following, performed by a processor for each point of the imaged zone:

determining of L' emissions, L'≤L, among the L successive emissions, of which the emission zones include the point considered, calculating of L'×N flight times, each flight time $t_{l,n}$ being time taken for an l-th plane wave, the emission zone of which includes the point considered, where 1≤l≤L', to be received by an n-th reception transducer, where 1≤n≤N, passing through the point considered according to a predetermined propagation mode, and coherent summing of L'×N instantaneous values taken respectively, by the L'×N measurement time signals received corresponding to the L' emissions determined, at the L'×N flight times calculated; and generating and displaying the imaged zone on a display.

10. An ultrasound probe device comprising:

a probe including M ultrasound emission transducers and N ultrasound reception transducers; and processing circuitry configured to:

control the M emission transducers for L successive emissions of ultrasound plane waves having L different successive emission angles in L emission zones;

control the N reception transducers so as to simultaneously receive, for a predetermined period, for each emission, N measurement time signals, measuring echoes due to reflections of the emission considered;

reconstitute an imaged zone by calculating, at each point of a plurality of predetermined points of the imaged zone, a value resulting from a processing of at least some of L×N measurement time signals received, the processing circuitry being further configured to perform the following processing operations for each point of the imaged zone:

determination of L' emissions, L'≤L, among the L successive emissions, of which the emission zones include the point considered, calculation of L'×N flight times, each flight time $t_{l,n}$ being time taken for an l-th plane wave, the emission zone of which includes the point considered, where 1≤l≤L', to be received by an n-th reception transducer, where 1≤n≤N, passing through the point considered according to a predetermined propagation mode, and coherent summing of L'×N instantaneous values taken, respectively, by the L'×N measurement time signals received corresponding to the L' emissions determined, at the L'×N flight times calculated; and the processing circuitry is further configured to generate and display the imaged zone on a display.

* * * * *